(12) United States Patent
Lajoie et al.

(10) Patent No.: US 6,555,650 B1
(45) Date of Patent: Apr. 29, 2003

(54) CYCLIC ANALOGS OF HISTATINS

(76) Inventors: Gilles Andre Lajoie, c/o Department of Chemistry University of Waterloo, Waterloo, Ontario (CA), N2L 3G1; Dyanne Brewer, c/o Department of Chemistry Universtiy of Waterloo, Waterloo, Ontario (CA), N2L 3G1

( * ) Notice: Subject to any disclaimer, the term of this patent is extended or adjusted under 35 U.S.C. 154(b) by 0 days.

(21) Appl. No.: 09/693,822

(22) Filed: Oct. 23, 2000

(30) Foreign Application Priority Data

Oct. 21, 1999 (CA) ............................................ 2285673

(51) Int. Cl.$^7$ ............................ A67K 38/12; C07K 7/00
(52) U.S. Cl. ...................... 530/317; 530/325; 530/326; 530/412; 514/13; 514/14; 435/254.1; 435/243
(58) Field of Search ................................ 530/317, 325, 530/326, 412; 514/13, 14; 435/254.1, 243

(56) References Cited

U.S. PATENT DOCUMENTS

| | | |
|---|---|---|
| 5,486,503 A | 1/1996 | Oppenheim |
| 5,631,228 A | 5/1997 | Oppenheim |
| 5,646,119 A | 7/1997 | Oppenheim |
| 5,696,078 A | 12/1997 | Oppenheim |
| 5,885,965 A | 3/1999 | Oppenheim |

OTHER PUBLICATIONS

S.E. Blondelle, R.A. Houghten, Annuals Reports in Medicinal Chemistry (1992), 27 159–168.
F.G. Oppenheim et al. J. Biol. Chem. (1986) 261(3) 1177–1182.
F.G. Oppenheim et al. J. Biol. Chem. (1986) 263(16) 7472–7477.
R.F. Troxler, F.G. Oppenheim et al. J. Dent. Res. (1990) 69(1), 2–6.
J.C. VanderSpek et al. Archs. Oral Biol. (1990) 35(2) 137–143.
C.F. Richardson et al. Archs. Oral Biol. (1993) 38(11) 997–1002.
Murakami, Y. et al. BBRC (1994) 198(1) 274–280.
B.J. MacKay et al. Infect. Immun. (1984) 44(3) 695–701.
J.J. Pollock et al. Infect. Immun. (1984) 44(3) 702–707.
A. Polak et al. Prog. Drug Res. (1991) 37 181–269.
P.A. Raj et al. J. Biol. Chem. (1990) 265(7) 3898–3905.
P.A. Raj et al. J. Biol. Chem. (1994) 269(13) 9610–9619.
Y. Zuo, et al. Gene (1995) 161 87–91.
R. E. W. Hancock, Lancet (1997) 349 418–422.
M. Gordon et al., J. Clinical Microbiol (1988) 26(9) 1874–1877.
E.J. Helmerhorst et al., J. Biol. Chem. (1999) 274(11) 7286–7291.
S.E. Koshlukova et al., J. Biol. Chem. (1999) 274(27) 18872–18879.
Y. Xu et al., Antimicrob. Agents Chemother. (1999) 43(9) 2256–2262.
M. Edgerton et al., J. Biol. Chem. (1998) 273(32) 20438–20447.
E. J. Helmerhorst et al., Biochem. J. (1997) 326 39–45.

*Primary Examiner*—Christopher S. F. Low
*Assistant Examiner*—Chih-Min Kam
(74) *Attorney, Agent, or Firm*—Ridout & Maybee LLP

(57) ABSTRACT

Cyclic analogues of histatin H-5, having from about 7–20 amino acid units exhibiting substantial homology to histatin H-5, and having a cyclic portion of from 5–16 of the amino acid units, have been found to exhibit enhanced bio-activity against a variety of different microorganisms. The cyclic structure is imparted by replacement of naturally occurring amino acids in histatin-5 sequences by, for example, by cysteine units, so as to cause cyclization through formation of disulfide bridges.

17 Claims, 1 Drawing Sheet

(SEQ ID NO: 28) H-1  $^{1}$Asp-pSer-His-Glu-Lys-Arg-His-His-Gly-Tyr-Arg-Arg-Lys-Phe-His-Glu-Lys-His-His-Ser-His-Arg-Glu-Phe-Pro-Phe-Tyr-Gly-Asp-Tyr-Gly-Ser-Asn-Tyr-Leu-Tyr-Asp-Asn$^{38}$ (SEQ ID NO: 29) H-2  $^{12}$Arg-Lys-Phe-His-Glu-Lys-His-His-Ser-His-Arg-Glu-Phe-Pro-Phe-Tyr-Gly-Asp-Tyr-Gly-Ser-Asn-Tyr-Leu-Tyr-Asp-Asn (SEQ ID NO: 30) H-3  $^{1}$Asp-Ser-His-Ala-Lys-Arg-His-His-Gly-Tyr-Lys-Arg-Lys-Phe-His-Glu-Lys-His-His-Ser-His-Arg-Gly-Tyr-Arg-Ser-Asn-Tyr-Leu-Tyr-Asp-Asn$^{32}$ (SEQ ID NO: 31) H-4  $^{12}$Arg-Lys-Phe-His-Glu-Lys-His-His-Ser-His-Arg-Gly-Tyr-Arg-Ser-Asn-Tyr-Leu-Tyr-Asp-Asn (SEQ ID NO: 39) H-5  $^{1}$Asp-Ser-His-Ala-Lys-Arg-His-His-Gly-Tyr-Lys-Arg-Lys-Phe-His-Glu-Lys-His-His-Ser-His-Arg-Gly-Tyr$^{24}$ (SEQ ID NO: 32) H-6  $^{1}$Asp-Ser-His-Ala-Lys-Arg-His-His-Gly-Tyr-Lys-Arg-Lys-Phe-His-Glu-Lys-His-His-Ser-His-Arg-Gly-Tyr-Arg$^{25}$ (SEQ ID NO: 33) H-7  Arg-Lys-Phe-His-Glu-Lys-His-His-Ser-His-Arg-Gly-Tyr (SEQ ID NO: 34) H-8  Lys-Phe-His-Glu-Lys-His-His-Ser-His-Arg-Gly-Tyr (SEQ ID NO: 35) H-9  Arg-Lys-Phe-His-Glu-Lys-His-His-Ser-His-Arg-Gly-Tyr-Arg (SEQ ID NO: 36) H-10 Lys-Phe-His-Glu-Lys-His-His-Ser-His-Arg-Gly-Tyr-Arg (SEQ ID NO: 37) H-11 Lys-Arg-His-His-Gly-Tyr-Lys-Arg (SEQ ID NO: 38) H-12 Lys-Arg-His-His-Gly-Tyr-Lys

Figure

SEQUENCE LISTING

```
<160> NUMBER OF SEQ ID NOS: 40

<210> SEQ ID NO 1
<211> LENGTH: 24
<212> TYPE: PRT
<213> ORGANISM: Homo sapiens

<400> SEQUENCE: 1

Asp Ser His Ala Lys Arg His His Gly Tyr Lys Arg Lys Phe His Glu
1               5                   10                  15

Lys His His Ser His Arg Gly Tyr
            20

<210> SEQ ID NO 2
<211> LENGTH: 23
<212> TYPE: PRT
<213> ORGANISM: Artificial Sequence
<220> FEATURE:
<223> OTHER INFORMATION: cyclic analogues of histatin

<400> SEQUENCE: 2

Ser His Ala Lys Arg His His Cys Tyr Lys Arg Lys Phe His Glu Lys
1               5                   10                  15

His His Ser His Arg Cys Tyr
            20

<210> SEQ ID NO 3
<211> LENGTH: 19
<212> TYPE: PRT
<213> ORGANISM: Artificial Sequence
<220> FEATURE:
<223> OTHER INFORMATION: cyclic analogues of histatin
```

```
<400> SEQUENCE: 3

Arg His His Cys Tyr Lys Arg Lys Phe His Glu Lys His His Ser His
1               5                   10                  15

Arg Cys Tyr

<210> SEQ ID NO 4
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 4

Arg His His Cys Tyr Lys Arg Lys Phe His Glu Lys His His Ser His
1               5                   10                  15

Arg Gly Cys

<210> SEQ ID NO 5
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 5

Arg His His Cys Tyr Lys Arg Lys Phe His Glu Lys His His Ser His
1               5                   10                  15

Arg Cys Tyr

<210> SEQ ID NO 6
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 6

Arg His His Cys Tyr Lys Arg Lys Phe His Glu Lys His His Ser His
1               5                   10                  15

Cys Gly Tyr

<210> SEQ ID NO 7
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 7

Arg His His Cys Tyr Lys Arg Lys Phe His Glu Lys His His Ser Cys
1               5                   10                  15

Arg Gly Tyr

<210> SEQ ID NO 8
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 8

Arg His His Cys Tyr Lys Arg Lys Phe His Glu Lys His His Cys His
```

-continued

```
                 1               5              10              15
Arg Gly Tyr

<210> SEQ ID NO 9
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 9

Arg His His Cys Tyr Lys Arg Lys Phe His Glu Lys His Cys Ser His
 1               5              10              15

Arg Gly Tyr

<210> SEQ ID NO 10
<211> LENGTH: 17
<212> TYPE: PRT
<213> ORGANISM: Artificial Sequence
<220> FEATURE:
<223> OTHER INFORMATION: cyclic analogues of histatin

<400> SEQUENCE: 10

Arg His His Cys Tyr Lys Arg Lys Glu Lys Cys His Ser His Arg Gly
 1               5              10              15

Tyr

<210> SEQ ID NO 11
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 11

Arg His His Gly Cys Lys Arg Lys Phe His Glu Lys His His Ser His
 1               5              10              15

Cys Gly Tyr

<210> SEQ ID NO 12
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 12

Arg His His Gly Tyr Lys Arg Lys Cys His Glu Lys His His Cys His
 1               5              10              15

Arg Gly Tyr

<210> SEQ ID NO 13
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 13

Arg His His Gly Tyr Lys Arg Cys Phe His Glu Lys His His Cys His
 1               5              10              15

Arg Gly Tyr
```

-continued

```
<210> SEQ ID NO 14
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 14

Arg His His Gly Tyr Lys Cys Lys Phe His Glu Lys His His Cys His
1               5                   10                  15

Arg Gly Tyr

<210> SEQ ID NO 15
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 15

Arg His His Gly Tyr Cys Arg Lys Phe His Glu Lys His His Cys His
1               5                   10                  15

Arg Gly Tyr

<210> SEQ ID NO 16
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 16

Arg His His Gly Cys Lys Arg Lys Phe His Glu Lys His His Cys His
1               5                   10                  15

Arg Gly Tyr

<210> SEQ ID NO 17
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 17

Arg His His Gly Cys Lys Arg Lys Phe His Glu Lys His His Ser Cys
1               5                   10                  15

Arg Gly Tyr

<210> SEQ ID NO 18
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 18

Arg His His Cys Tyr Lys Arg Lys His His Glu Lys His His Cys His
1               5                   10                  15

Arg Gly Tyr

<210> SEQ ID NO 19
<211> LENGTH: 18
<212> TYPE: PRT
```

```
<213> ORGANISM: Artificial Sequence
<220> FEATURE:
<223> OTHER INFORMATION: cyclic analogues of histatin

<400> SEQUENCE: 19

Arg His His Cys Tyr Lys Arg Lys Phe His Glu Lys His His Cys His
1               5                   10                  15

Arg Gly

<210> SEQ ID NO 20
<211> LENGTH: 17
<212> TYPE: PRT
<213> ORGANISM: Artificial Sequence
<220> FEATURE:
<223> OTHER INFORMATION: cyclic analogues of histatin

<400> SEQUENCE: 20

Arg His His Cys Tyr Lys Arg Lys Phe His Glu Lys His His Cys His
1               5                   10                  15

Arg

<210> SEQ ID NO 21
<211> LENGTH: 16
<212> TYPE: PRT
<213> ORGANISM: Artificial Sequence
<220> FEATURE:
<223> OTHER INFORMATION: cyclic analogues of histatin

<400> SEQUENCE: 21

Arg His His Cys Tyr Lys Arg Lys Phe His Glu Lys His His Cys His
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: cyclic analogues of histatin

<400> SEQUENCE: 22

Arg His His Cys Tyr Lys Arg Lys Phe His Glu Lys His His Cys
1               5                   10                  15

<210> SEQ ID NO 23
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 23

Arg His His Cys Tyr Lys Arg Lys Phe His Glu Lys His His Cys His
1               5                   10                  15

Arg Gly Tyr

<210> SEQ ID NO 24
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 24

Arg His His Cys Tyr Lys Arg Lys Phe His Glu Lys His His Cys His
1               5                   10                  15
```

Arg Gly Tyr

<210> SEQ ID NO 25
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 25

Arg His His Cys Trp Lys Arg Lys Phe His Glu Lys His His Cys His
1               5                   10                  15

Arg Gly Tyr

<210> SEQ ID NO 26
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 26

Arg His His Cys Tyr Lys Arg Lys Cys His Glu Lys His His Cys His
1               5                   10                  15

Arg Cys Tyr

<210> SEQ ID NO 27
<211> LENGTH: 19
<212> TYPE: PRT
<213> ORGANISM: Artificial Sequence
<220> FEATURE:
<223> OTHER INFORMATION: cyclic analogues of histatin

<400> SEQUENCE: 27

Arg His His Lys Tyr Lys Arg Lys Phe His Glu Lys His His Glu His
1               5                   10                  15

Arg Gly Tyr

<210> SEQ ID NO 28
<211> LENGTH: 38
<212> TYPE: PRT
<213> ORGANISM: Homo sapiens
<220> FEATURE:
<221> NAME/KEY: misc_feature
<222> LOCATION: (2)..(2)
<223> OTHER INFORMATION: phosphoserine

<400> SEQUENCE: 28

Asp Xaa His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
        35

<210> SEQ ID NO 29
<211> LENGTH: 27
<212> TYPE: PRT
<213> ORGANISM: Homo sapiens

<400> SEQUENCE: 29

Arg Lys Phe His Glu Lys His His Ser His Arg Glu Phe Pro Phe Tyr
1               5                   10                  15

Gly Asp Tyr Gly Ser Asn Tyr Leu Tyr Asp Asn
            20                  25

<210> SEQ ID NO 30
<211> LENGTH: 32
<212> TYPE: PRT
<213> ORGANISM: Homo sapiens

<400> SEQUENCE: 30

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 31
<211> LENGTH: 21
<212> TYPE: PRT
<213> ORGANISM: Homo sapiens

<400> SEQUENCE: 31

Arg Lys Phe His Glu Lys His His Ser His Arg Gly Tyr Arg Ser Asn
1               5                   10                  15

Tyr Leu Tyr Asp Asn
            20

<210> SEQ ID NO 32
<211> LENGTH: 25
<212> TYPE: PRT
<213> ORGANISM: Homo sapiens

<400> SEQUENCE: 32

Asp Ser His Ala Lys Arg His His Gly Tyr Lys Arg Lys Phe His Glu
1               5                   10                  15

Lys His His Ser His Arg Gly Tyr Arg
            20                  25

<210> SEQ ID NO 33
<211> LENGTH: 13
<212> TYPE: PRT
<213> ORGANISM: Homo sapiens

<400> SEQUENCE: 33

Arg Lys Phe His Glu Lys His His Ser His Arg Gly Tyr
1               5                   10

<210> SEQ ID NO 34
<211> LENGTH: 12
<212> TYPE: PRT
<213> ORGANISM: Homo sapiens

<400> SEQUENCE: 34

Lys Phe His Glu Lys His His Ser His Arg Gly Tyr
1               5                   10

<210> SEQ ID NO 35
<211> LENGTH: 14
<212> TYPE: PRT
<213> ORGANISM: Homo sapiens

<400> SEQUENCE: 35

Arg Lys Phe His Glu Lys His His Ser His Arg Gly Tyr Arg
1               5                   10

```
<210> SEQ ID NO 36
<211> LENGTH: 13
<212> TYPE: PRT
<213> ORGANISM: Homo sapiens

<400> SEQUENCE: 36

Lys Phe His Glu Lys His His Ser His Arg Gly Tyr Arg
1               5                   10

<210> SEQ ID NO 37
<211> LENGTH: 8
<212> TYPE: PRT
<213> ORGANISM: Homo sapiens

<400> SEQUENCE: 37

Lys Arg His His Gly Tyr Lys Arg
1               5

<210> SEQ ID NO 38
<211> LENGTH: 7
<212> TYPE: PRT
<213> ORGANISM: Homo sapiens

<400> SEQUENCE: 38

Lys Arg His His Gly Tyr Lys
1               5

<210> SEQ ID NO 39
<211> LENGTH: 24
<212> TYPE: PRT
<213> ORGANISM: Homo sapiens

<400> SEQUENCE: 39

Asp Ser His Ala Lys Arg His His Gly Tyr Lys Arg Lys Phe His Glu
1               5                   10                  15

Lys His His Ser His Arg Gly Tyr
            20

<210> SEQ ID NO 40
<211> LENGTH: 14
<212> TYPE: PRT
<213> ORGANISM: Artificial Sequence
<220> FEATURE:
<223> OTHER INFORMATION: cyclic analogues of histatin

<400> SEQUENCE: 40

Cys Tyr Lys Arg Lys Phe His Glu Lys His His Cys His Arg
1               5                   10
```

CYCLIC ANALOGS OF HISTATINS

FIELD OF THE INVENTION

This invention relates to novel bio chemical compounds and compositions having pharmaceutical and medical activities, and to processes for their preparation and use. More specifically, it relates to novel peptide compounds and compositions of the histatin type, which exhibit antimicrobial properties.

BACKGROUND OF THE INVENTION AND PRIOR ART

Antimicrobial peptides have been found in a variety of organisms. Among the most studied are the magainins from the skins of amphibians, the cecropins from the moth cecropia, melittin and bombolitin from bee venom. In all cases these are cationic peptides reportedly exerting their antibacterial action by altering the membrane permeability. These peptides have an amphiphatic α-helical structure which is critical for their activity (1). Another class of potent antimicrobial peptides, the defensins, was isolated from mammalian phagocytic cells. Defensins have a broad range of activity against bacteria, fungi, viruses and tumour cells and are considered to be important in the host non-immune defense system. X-ray and NMR analysis has revealed that the defensins assume an antiparallel β-sheet conformation. It has also been shown that defensins form voltage dependent channels in model lipid bilayer.

Another class of antimicrobial peptides was recently identified in human saliva. They were originally called histidine-rich peptides (HRP)(2) and later referred to as histatins (3). Twelve members of this family have been characterized (3,4). Histatins are secreted by the parotid and submandibular glands and constitute 3 percent dry weight of saliva (2). The three major forms are histatin-1 (H-1), histatin-3 (H-3), and histatin-5 (H-5) which are 38, 32 and 24 amino acids peptides, respectively and have highly homologous sequence, as depicted in the accompanying Figure. H-1 and H-3 are derived from different genes (5), whereas H-5 is proteolytically derived from H-3. Other members of this family are proteolytically produced from the three main forms although the enzyme(s) responsible for this processing is presently unknown. The smaller members have reduced antimicrobial activities. H-1, H-3 and H-5 contain several basic residues including seven conserved histidines. Homologous histatin sequences have also been isolated from the saliva of other primates.

These peptides are highly basic (cationic), non-amphiphilic and show no homology to other known proteins. Histatins have been implicated in several biological functions. Histatin-3 and -5 possess antibacterial and antifungal properties at physiological concentrations and may play an important role in the non-immune oral host defense system.

Histatins have been shown to have a number of different biological activities. A phosphorylated member, histatin-1, selectively adsorbs to hydroxylapatite and enamel powder, possibly acting as a precursor of the acquired enamel pellicule (6). More recently, H-5 has been shown to act synergistically with epidermal growth factor (EGF) to promote rabbit chondrocyte proliferation (7). Patents describing the use of histatins for wound healing, and bond and periodontal tissue regeneration have also appeared (8–10).

It has been reported that H-1, H-3 and H-5 possess potent antimicrobial properties against bacteria (11) and fungi (12) in a concentration dependent manner at physiological concentrations. The most potent, H-5, has a minimum inhibitory concentration (MIC) of 10 $\mu$g/ml against $C.$ $albicans$ (12). This value compares favorably with the widely used antifungal agent ketoconazole, which is an inhibitor of lanosterol C-14 demethylase, an important enzyme in the biosynthesis of ergosterol (13). The mode of action of histatin is still unknown.

In the one of the earliest structure-activity relationship (SAR) studies of histatins published to date, Raj et al. reported that the C-terminal fragment is most important and that a minimum of 16 amino acids (H-$5^{8-24}$) were required for activity against $C.$ $albicans$ (14). Because of the large number of positive charge on H-$5^{8-24}$, these authors suggested that histatins interact with the polar head groups of the phospholipid membranes, but only weak experimental evidence supports this hypothesis. Raj and co-workers also showed by CD and NMR that H-$5^{8-24}$ has no structure in H$_2$O but adopts an extended α-helical conformation in trifluoroethanol (TFE) or in DMSO (14). The same group also reported that the H-$5^{8-24}$ fragment has α-helical character in the presence of DMPC vesicles, and that the conformation is pH independent (15). More recenty. Oppenheim and co-workers (16) have produced by recombinant methods an H-3 peptide mutant in which the central region of H-$3^{(13-24-13-24)}$ was tandemly repeated. At very low concentrations, this H-$3^{(13-24-13-24)}$ fusion peptide was apparently more active than H-3 in the candicidal assay (16).

The conformation of histatin-5 in water or in the presence of its biological targets has not been firmly established.

It is an object of the present invention to provide novel histatin analogs having improved microbiocidal properties.

SUMMARY OF THE INVENTION

The present invention derives from our discoveries that the most bioactive conformation of histatin peptides involves their adoption of a hairpin loop conformation in the region of positions 8–24 of H-5, likely around $E^{16}$-$K^{17}$ and that histatin peptides are reasonably tolerant to amino acid replacement. Accordingly, we have found that the introduction of substantially permanent loop structures into H-5 peptide compounds, to provide cyclic analogs of histatins, leads to compounds having much more potent activity than H-5 against a variety of different microorganisms. Since some amino acid replacement can be tolerated in H-5 without significant loss of activity, the introduction of replacement amino acids at appropriate locations in the chain so as to form chemical bridges between themselves (e.g. disulphide bonds between introduced cysteine residues) can be accomplished. In this way, the loop or cyclic structure is substantially permanently imparted to the compounds, subject only to the normal chemical stability of the loop-forming bonds between the replacement amino acids (mutations). The result is a family of novel cyclic peptides analogous to H-5, but having much greater antimicrobial activity than H-5, as set out in the specific examples below.

Thus according to the present invention, from one aspect, there is provided cyclic analogues of histatin H-5 having from about 7–20 amino acid units exhibiting substantial homology to histatin H-5, and having a cyclic portion of from 5–16 of said amino acid units.

The bioactive conformation of H-3 is not an extended helix as inferred by previous reports, but a loop or cyclic structure. Although this loop structure motif is unusual for antimicrobial peptides, it has been observed in brevenins from frog skin or of bactenecins from bovine neutrophils (17).

BRIEF REFERENCE TO THE DRAWING

The single FIGURE of accompanying drawings illustrates known amino acid sequences of histatins 1 to 12, based upon prior art publication (Ref. 4, Troxler et.al.). In the drawing and throughout the specification and claims, the standard, internationally accepted code letters for individual amino acids are used (Pse=phosphoserine).

DESCRIPTION OF THE PREFERRED EMBODIMENTS

The term "substantial homology" as used herein is intended to mean sequences of amino acids which have at least 60% and preferably at least 80% identity of unit and sequence with the natural product histatin H-5. It has been found that there is considerable tolerance of substitution of individual amino acids in histatins, without substantial loss of activity.

Histatins H-5$^{8-24}$, H-5 and H-3 and analogs and mutations thereof an be prepared by standard methods of peptide synthesis. The analogs may comprise D-amino acid analogs, L-amino acid analogs, and analogs incorporating random or preselected mixtures of D- and L-amino acids, in the predetermined, defined sequence. Chemical syntheses for step-by-step assembly of peptides using predetermined sequences of amino acid starting units, with appropriate chemical protection and deprotection steps, are well known and can be adopted in preparation of analogs according to the present invention. Preferred syntheses use solid phase peptide synthesis technology, e.g using 4-alkoxybenzyl alcohol or 2-chlorotrityl chloride solid support resins, on a continuous flow synthesizer. They can also be prepared by the batch mode method as originally described by Merrifield. The peptides can also be made by solution methods or by a combination of liquid phase and solid phase methods. The N-amino group of the amino acid is suitably protected with a base labile fluorenylmethoxycarbonyl (FMOC) group or a t-butyloxycarbonyl (BOC) group during synthesis while its acid group is reacted. Tyrosine, serine, threonine, glutamic acid and aspartic acid side groups are suitably protected with t-butl groups during chain extension. Potential racemization of the imidazole ring of histidine is suitably blocked by use of an N-trityl group. The reactivity of cysteine side chains can also be masked with a trtyl group. Arginine residues are appropriately protected at their N-terminus with pentamethylchroman-6-sulfonyl (PMC) groups. Lysine is suitably protected with BOC groups.

Coupling of amino acids is suitably achieved by activating the first amino acid with benzotriazol-1-yloxytris (dimethylamino)phosphonium hexafluorophosphate (BOP) and 1-hydroxybenzotriazole, to form the active ester. Activators such as N-methylmorpholine (NMM) or collidine may also be used to assist in the reaction. Other common coupling agents such as DCC, HBTU, HATU etc can be used. All these peptide synthesis techniques, and equivalents and alternatives to them, are within the skill of the art and well known to skilled peptide chemists.

The peptides so formed may be cleaved from their solid synthesis supports by standard protocol using trifluoroacetic acid and appropriate scavengers, and the blocking groups by standard procedures. The peptides so formed can be purified by reverse phase HPLC.

Peptides containing only L-amino acids can be obtained by chemical synthesis or by DNA recombinant techniques. Other peptides with D-amino acids or with lactam groups as the means for providing cyclization are prepared by chemical synthesis or by semi-synthesis using enzymes. The synthetic protocol (couplings, deprotection and cleavage times) may be optimized for a continuous flow synthesizer (Millipore 9050) using Fmoc-chemistry. Electrospray mass spectrometer (ESMS) is used to detect deletions and other side reactions. Purification to homogeneity is achieved by reverse phase HPLC using a C-18 column. In general, overall yields of pure peptides are greater than 60% (as high as 90%) and quantities >100 mg are routinely obtained.

To prepare the cyclic peptides of the present invention, it is necessary to make at least one amino acid substitution, as compared with histatin H-5. The natural product contains within the region forming the active loop structure lysine groups, which in one embodiment of the invention can be used as points of cyclization, utilizing their free amino groups in reaction with free carboxyl of glutamic acid to form a lactam (amide) link and result in ring formation. However, the glutamic acid residue naturally present in histatin H-5, at position 16, should preferably be left intact and not utilized in the cyclization, since it appears to have a role in the activty of the final compounds. Accordingly, it is preferred to introduce a glutamic acid as a substitute amino acid group for purposes of reaction with lysine to form the cyclized form, via a lactam group. Lysine, for participation in the cyclization reaction, can also be introduced as a substitute group, or alternatively one can make use of one of the lysine groups naturally present.

An alternative and preferred amino acid substitution into the histatin analogs for cyclization purposes in the present invention is cysteine, which can readily be introduced by known methods, in place of any of the naturally occurring amino acids of histatin. Cysteine residues in the peptide chain readily form disulfide bridges between themselves so as to impart the necessary cyclic structures. While the bonds are chemically reversible, they are sufficiently permanent to meet the criteria for compounds of the present invention. As alternatives to cysteine, there can be used other thiol-containing amino acids e.g. homocysteine or penicillamine. Bicyclic analogues with two disulfide bridges or one disulfide and one lactam bond can also be made. Head-to-tail cyclization can also be made. Cyclization can also be done by other chemical means, e.g. by thioether linkage.

Peptides containing cysteine substitutions and cyclized through disulfide groups can be made by air oxidation of the free linear peptide in a 0.1 molar solution of ammonium bicarbonate, with selective protection of the cysteine. Lactam-cyclized peptides can be prepared by the selective removal of the Aloc/Allyl Lys and Glu side chain protecting groups under mild conditions with a Pd(0) catalyst while the peptide is still attached to the resin and the other side chains remain protected. An amide bond can then be formed between the side chains using (benzotriazolyloxy) tris (dimethylamino) phosphonium hexafluorophosphate (pyBOP0 and HOBt as coupling reagents, or with other common coupling reagents. Then the cyclized peptide can be cleaved from the resin and purified by reverse phase HPLC.

Potential applications in health care industry include orally administrable formulations (tablets, capsules, lozenges, chewing gums, etc, with standard, known fillers, extenders, excipients and the like), tooth paste, mouth wash products, other dental care products, antiperspirant, coatings on protective device for wound dressing (e.g. BandAid®). Other potential medical applications in medicine include wound healing and tissue regeneration after surgery or accidental trauma.

SPECIFIC DESCRIPTION OF MOST PREFERRED EMBODIMENTS

EXAMPLE 1

COMPOUNDS WITH DISULFIDE BRIDGES

Using the standard techniques of peptide synthetic chemistry described above, a series of histatin H-5 analogs according to the present invention was prepared, the amino acid sequences of which are listed below in Table 1, along with that of the naturally occurring H-5. Each possessed substantial homology with H-5 from position 5 to position 19 of the natural H-5, and in some cases beyond. Each contained two cysteine groups C in replacement of two naturally occurring amino acids of H-5, from 5 to 14 amino acids apart, and cyclized as described above to insert disulfide bridges between the two cysteine groups C and create cyclic peptide structures having loops or rings from 7 to 16 amino acids in length. In some cases, e.g.Db2-121, additional deletions were made so that the amino acid chain was shorter than that of either of H-5 or H-3. In some cases also, additional substitutions were made, but leaving the product within the range of substantial homology with H-5.

The compounds of Table 1 were tested for fungistatic activity with an assay based on the work of Gordon, Lapa et.al. (18) with the nonpathogenic yeast S. cerevisiae in which ketoconazole is used as control. A semisolid is prepared to which is added serial dilutions of peptide. This antifungal agar is distributed in a well plate, and the S. Cerevisiae inoculum is then added to each well. Both ketokonoazole and H-5 are used as positive controls and buffer is used as a control blank. Minimum inhibitory concentration MIC, i.e. the concentration of the peptide under test which prevents growth, as observed visually, is recorded for each sample so that low values of MIC indicate potent antifungal compounds.

More specifically, stock peptide solutions (600 microliters or 1 ml) were prepared to 10 times the final concentration of the most concentrated test sample in a sodium phosphate buffer (0.01 M0, pH 7.4). Peptide concentrations were determined by UV absorbance at $\lambda=275$. Control blanks were also prepared using 1 ml buffer Five serial dilutions were made in sterile culture tubes with buffer to create a range of peptide concentrations. The final volume in each tube was either 300 microliter or 1 ml. Agar medium (2.7 or 4.5 ml) was added to each tube and mixed. Aliquots (1 ml) of each were added to a 24 well plate to give 6 different concentrations of each peptide per plate. Each plate had a row of control blanks and a row of a positive control (ketoconazole). A stock solution (10 mg/mL DMSO) was diluted 1:49 with buffer. A range of final concentrations of 20 to 0.16 micrograms/ml was tested. In addition, in later analog assays, H-5 was included as a positive peptide control. Histatin 5 was tested in a range from 200 micromolar to 6.3 micromolar. Other analogs were tested at concentrations anywhere from 200 $\mu$M down to 0.14 $\mu$M ubtil the analog with lowest MIC concentration was identified.

S. cerevisiae cells grown overnight were centrifuged and washed with a 0.85% saline solution, three times. Cell concentration was adjusted to 85% transmission at $\lambda=530$ with saline solution. Cells were further diluted 1:19. Inoculant (10 microL) was added to the peptide-containing medium. The cells were incubated on this medium for 24 hours at 37° C. The fungistatic MIC for these compounds was defined as the minimum concentration required to achieve 100% inhibition after 24 hours.

The results are included in the following Table.

| | | |
|---|---|---|
| Db2-180 (14) | Arg His His Gly Tyr Lys Cys Lys Phe His Glu Lys His His Cys His Arg Gly Tyr | 1.25–2.5 |
| Db2-179 (15) | Arg His His Gly Tyr Cys Arg Lys Phe His Glu Lys His His Cys His Arg Gly Tyr | 2.5–5 |
| Db2-178 (16) | Arg His His Gly Cys Lys Arg Lys Phe His Glu Lys His His Cys His Arg Gly Tyr | 2.5–5 |
| Db3-11 (17) | Arg His His Gly Cys Lys Arg Lys Phe His Glu Lys His His Ser Cys Arg Gly Tyr | 2.5–5 |
| Db3-13 (18) | Arg His His Cys Tyr Lys Arg Lys His His Glu Lys His His Cys His Arg Gly Tyr | 2.6–5.1 |
| Db3-19 (19) | Arg His His Cys Tyr Lys Arg Lys Phe His Glu Lys His His Cys His Arg Gly | 1.3–2.6 |
| Db3-15 (20) | Arg His His Cys Tyr Lys Arg Lys Phe His Glu Lys His His Cys His Arg | 2.6–5.2 |
| Db3-25 (21) | Arg His His Cys Tyr Lys Arg Lys Phe His Glu Lys His His Cys His | >5.2 |
| Db3-30 (22) | Arg His His Cys Tyr Arg Lys Phe His Glu Lys His His Cys | >5.2 |
| Db3-35 (23) | Arg His His Cys Tyr Lys Arg Lys Phe His Glu Lys His His Cys His Arg Gly Tyr | 1.3–2.5 |
| Db3-53 (24) | Arg His His Cys Tyr Lys Arg Lys Phe His Glu Lys His His Cys His Arg Gly Tyr | >5 |
| Db3-67 (25) | Arg His His Cys Trp Lys Arg Lys Phe His Glu Lys His His Cys His Arg Gly Tyr | 0.67–1.34 |
| Ketoconazole | | 4.7 | substantial improvement of activity can be obtained. Db2-121 (Gly$^9$->Cys, Ser$^{20}$->Cys) was found to be most potent with a MIC of 0.3 $\mu$M which is approximately 100 times more potent than H-5 and 10 times more potent than ketoconazole against S. cerevisiae. Importantly, a similar activity profile for Db2-121 is observed against C. albicans and against three different bacteria; IS. Aureus (Gr+). E. coli (Gr−) and β. Magatenum (Gr+). From studies of the cysteine scan, it is quite evident that loop stabilization by correct disulfide cyclization is one way to enhance the activity of H-5 and related peptides. Db2-121 is 19 amino acids long and therefore shorter than H-5 or H-3. Additional deletions at the C-terminal (Db2-19 and Db2-15) can be done but with small loss of activity. A disulfide containing peptide with D-amino acids at each end of the chain was prepared and evaluated for biological activty—compound Db3-35. This type of modification often increases the stability of peptides towards proteolytic degradation. As often seen with other peptides, loop stabilization may also increase the proteolytic stability.

A hypotonic assay based on the work of Helmerhorst et.al (19) was used to determine the loss of cell viability of C. albicans in the presence of peptide compounds of the present invention. This protocol involves incubating the peptide and cells in a low osmolality solution for 1,5 hours with constant mixing. Standard plate count procedure is then followed to determine the concentration of viable cells remaining. By determining the cell concentration levels in negative control wells, the % loss of cell viability due to the presence of the peptide is determined. MICs for H-5 and H-5$^{8-24}$ were similar to those reported against C. albicans.

Preliminary toxicity studies indicate that at least one of the cyclic analogs tested has no acute toxicity in mice (5 mice) after injection of a rather massive dose (15 mg/kg) in the intraperitoneal cavity.

EXAMPLE 2

BICYCLIC PEPTIDE WITH DISULFIDE BRIDGES

We also synthesized Db2-100, a peptide which contains two disulfide bonds (giving a bicyclic peptide), by selective protection of the cysteine. In this preparation, the first set of protecting groups, the trityl groups, were removed and oxidized as described above. The second set of protecting groups, the acetamidomethyl (Acm), were removed with iodine, and the resulting peptide purified by RP HPLC and air oxidized to form the second disulfide bridge.

Peptide Db2-100 had the following sequence:

Arg His His Cys Tyr Lys Arg Lys Cys His Glu Lys His His Cys His Arg Cys Tyr (SEQ ID NO:26)

The bicyclic structure is even more conformationally constrained that the other analogs and the compound has retained its biological activity—MIC range determined as described for the compunds of Example 1 is 0.63–1.25.

EXAMPLE 3

CYCLIC PEPTIDE WITH LACTAM (AMIDE) BOND

To demonstrate that the cyclic structure of the peptide, and not the presence of the disulfide itself, is determinant for optimal activity, we prepared Db3-41 a peptide analog of db2-121 in which the cyclization is effected by means of an amide bond (lactam) between the side chain of a glutamic acid and lysine, by methods described above. The glutamic acid is at position 9 and lysine at position 20. In this case, where an orthogonal protection scheme was required, the allyloxycarbonyl (Aloc) protecting group was used for lysine, and the allyl group was used for glutamic acid.

The full sequence of Db3-41 is Arg His His Lys Tyr Arg Lys Phe His Glu Lys His His Glu His Arg Gly Tyr. (SEQ ID NO:27)

The fungistatic activity of Db3-41 is comparable to Db2-121, i.e. MIC range ($\mu$m) 0.55–1.1.

References

1. S. E. Blondelle, R. A. Houghten, Annuals Reports in Medicinal Chemistry (1992), 27 159.
2. F. G. Oppenheim et al. J. Biol. Chem. (1986) 261 1177.
3. F. G. Oppenheim et al. J. Biol. Chem. (1988) 263 7472.
4. R. F. Troxler, F. G. Oppenheim et al. J. Dent. Res. (1990) 1 2.
5. J. C. VanerSpek et al. Arch. Oral Biol. (1990) 35 137.
6. C. F. Richardson et al. Arch. Oral Biol. (1993) 38 997.
7. Murakami, Y. et al. BBRC 198 274.
8. S. Taniguchi et al. JP 94-76628 940322; CAS:123;350366.
9. N. Matsuda et al. JP 93-98530 930331; CAS:122:89439.
10. A. Takemura et al. JP 93-45998 930210; CAS:121:308303.
11. B. J. MacKay et al. Infect. Immun. (1984) 44 695.
12. J. J. Pollock et al. Infect. Immun. (1984) 44 702.
13. A. Polaketal. Prog. Drug Res. (1991) 37 181.
14. P. A. Raj et al. J. Biol. Chem. (1990) 265 3898.
15. P. A. Raj et al. J. Biol. Chem. (1994) 289 9610.
16. Y. Zuo. F. G. Oppenheim et al. Gene (1995) 161 87.
17. E. R. Hancock The Lancet 39, 418 (1997).
18. M. Gordon et al., J. Clinical Microbiol. (1988) 26 1874.
19. E. J. Helmerhorst et al., J. Biol. Chem. (1999) 274 7286.

---

What is claimed is:

1. A synthetic peptide:
   having 15 to 20 amino acid units including a 15 amino acid region which is at least 78% homologous in amino acid sequence to a 15 amino acid portion of SEQ ID NO:1;
   between 8 to 12 of said 15 to 20 amino acid units forming a cyclic structure;
   said cyclic structure including a Glu Lys pair;
   said Glu Lys pair consisting of a glutamic acid residue and a lysine residue;
   said glutamic acid residue located immediately adjacent and on the amino side of a lysine residue;
   said peptide further having at least three amino acid units on both sides of said Glu Lys pair;
   said cyclic structure having at least a first and second point of cyclization, with said first point of cyclization being distinct from and located on one side of said Glu Lys pair and said second point of cyclization being distinct from and located on another side of said Glu Lys pair;
   each said point of cyclization being an amino acid having a side chain adapted to form a link with the amino acid side chain of the other point of cyclization;
   said points of cyclization being adapted to interact to form said cyclic structure;
   said points of cyclization being selected from lysine, glutamic acid and cysteine;
   said first point of cyclization being lysine when said second point of cyclization is glutamic acid; and said first point of cyclization being cysteine when said second point of cyclization is cysteine.

2. The peptide of claim 1 wherein said first point of cyclization is lysine and said second point of cyclization is glutamic acid.

3. The peptide of claim 1 wherein both said first and second point of cyclization are cysteine.

4. The peptide of claim 1 wherein the 15 amino acid region is at least 85% homologous in amino acid sequence to a portion of SEQ ID NO:1 of the same length.

5. The peptide of claim 1 further including an additional lysine residue located 3 positions to the amino side of said glutamic acid residue.

6. The peptide of claim 5 further including an arginine residue immediately adjacent and on the amino side of said additional lysine residue.

7. The peptide of claim 6 further including a third lysine residue immediately adjacent and on the amino-terminal side of said arginine residue.

8. The peptide of claim 1 further including a histidine residue immediately adjacent and on the carboxy side of said lysine residue.

9. The peptide of claim 8 further including a second histidine residue immediately adjacent and on the carboxy side of said histidine residue.

10. The peptide of claim 1 selected from the group consisting of SEQ ID NO:8, 9, 13, 14, 15, 16, 17, 18, 19, 20, 23, and 25.

11. A peptide of claim 1 selected from the group consisting of SEQ ID NO:8, 13, 14, 19, 23 and 25.

12. The peptide of claim 1 selected from the group consisting of SEQ ID NO:8 and 25.

13. The peptide of claim 1 having an amino acid sequence including Cys Tyr Lys Arg Lys Phe His Glu Lys His His Cys His Arg (SEQ ID NO:40).

14. The peptide of claim 13 having the amino acid sequence of SEQ ID NO:8.

15. The peptide of claim 1 wherein said points of cyclization are separated by at least 6 amino acids.

16. The peptide of claim 15 wherein said points of cyclization are separated by at least 9 amino acids.

17. The peptide of claim 15 wherein said points of cyclization are separated by 10 amino acids.

* * * * *